Figure 1:
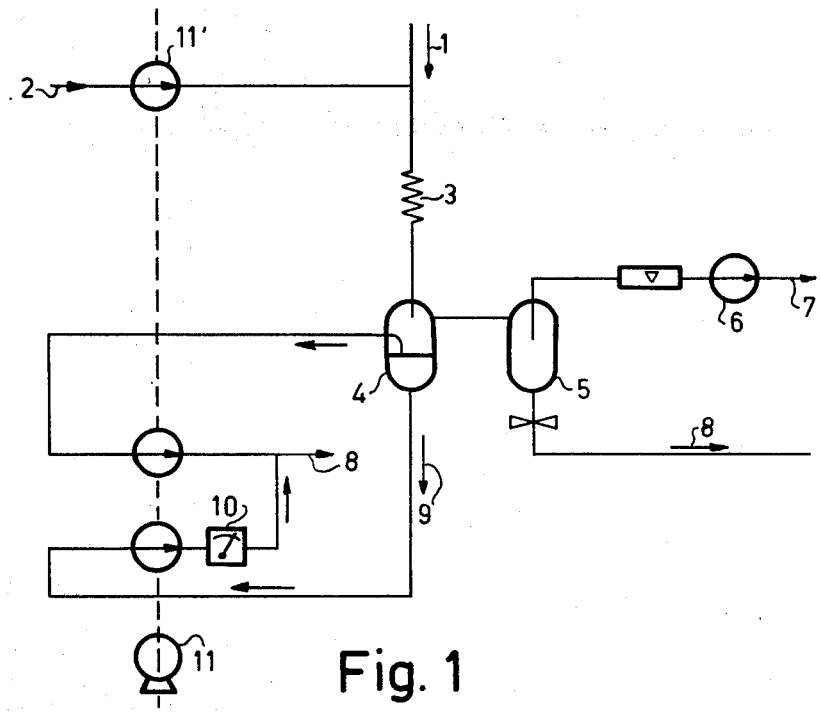

United States Patent [19]
Brouwer

[11] 3,977,254
[45] Aug. 31, 1976

[54] APPARATUS FOR SAMPLING FOR USE IN A CONTINUOUS DETERMINATION OF A COMPONENT IN A GAS MIXTURE

[75] Inventor: Harm Jan Brouwer, Eindhoven, Netherlands

[73] Assignee: U.S. Philips Corporation, New York, N.Y.

[22] Filed: Oct. 2, 1975

[21] Appl. No.: 618,770

[30] Foreign Application Priority Data
Oct. 22, 1974 Netherlands.................... 7413796

[52] U.S. Cl. ................................. 73/422 R; 55/270
[51] Int. Cl.² ........................................... G01N 1/00
[58] Field of Search ............. 55/40, 43, 48, 55, 56, 55/57, 71, 270; 73/421, 421.5, 422

[56] References Cited
UNITED STATES PATENTS

| | | |
|---|---|---|
| 3,255,575 | 6/1966 | Roberts.................................. 55/55 |
| 3,446,077 | 5/1969 | Sanford et al. .................... 73/421.5 |
| 3,581,473 | 6/1971 | Ririe, Jr. et al....................... 55/270 |
| 3,641,821 | 2/1972 | Neuberger et al. ............ 73/421.5 R |

Primary Examiner—Bernard Nozick
Attorney, Agent, or Firm—Frank R. Trifari; Carl P. Steinhauser

[57] ABSTRACT

Sampling apparatus in which a gas component which is to be analytically determined is absorbed in a liquid, the liquid and the gas are separated from one another and the liquid is analyzed. The apparatus includes a device in which fluctuating evaporation losses are compensated. This is of particular importance for determining low concentrations, the relevant gas being absorbed in a comparatively small quantity of liquid.

1 Claim, 2 Drawing Figures

APPARATUS FOR SAMPLING FOR USE IN A CONTINUOUS DETERMINATION OF A COMPONENT IN A GAS MIXTURE

The invention relates to an apparatus for continuous sampling for use in a continuous determination of a gaseous component in a gas mixture.

The Technicon folder "Specific Air Pollutants" describes such an apparatus in which at least the component to be determined is absorbed in a liquid, determination being then effected on the resulting doped liquid.

In the said apparatus it is not necessary for the component to be absorbed quantitatively; it is sufficient for a constant fraction to be absorbed.

The said apparatus comprises an absorption member to which a constant stream of sample gas and a constant stream of absorption liquid are supplied and in which the two streams are brought into contact and a passage to a liquid separator, which separator has a constant liquid level by means of a suction opening, provision being made of a gas outlet above the liquid level and of a liquid outlet below this level, whilst care is taken to ensure that at any instant the discharge to the liquid separator is less than the supply, the liquid which is discharged from the separator at a constant flow rate being supplied to a detector. The absorption liquid as a rule is a solvent in which one or more reagents have been dissolved. The detector can operate on any suitable principle which requires the sample to be supplied in the liquid phase. This principle may be electrochemical, such as amperometric or potentiometric, but also spectrophotometric or fluorimetric, etc.

The said apparatus in general operates satisfactorily, however, when measuring very low concentrations, in which process large quantities of gas are contacted with comparatively small quantities of absorption liquid, large fluctuations in the measuring results are observed owing to fluctuations of the vapour pressure of the solvent of the absorption liquid for the gas mixture to be analysed which enters the absorption member. This means that a part of the absorption liquid, which part fluctuates with the dew-point of the gas mixture, evaporates in the gas stream and is lost in the separator.

It is an object of the present invention to eliminate the said measuring fluctuations.

The apparatus according to the invention is characterized in that the liquid separator comprises two reservoirs which communicate with one another both for the gas phase and for the liquid phase, the supply conduit from the absorption member opening into one reservoir whilst the suction opening of the level-regulator is located in the other reservoir, to which latter reservoir a constant stream of pure solvent of the absorption liquid is supplied, the constant discharge of liquid to be analyzed to the detector being smaller than the overall supply but greater than the supply from the absorption member.

It will be appreciated that by means of the said communicating vessels any solvent of the absorption liquid which may evaporate and is entrained by the gas stream is replenished so that the measured concentration always is such as if no solvent had evaporated owing to a fluctuating dew-point of the measuring gas.

Figure 2:
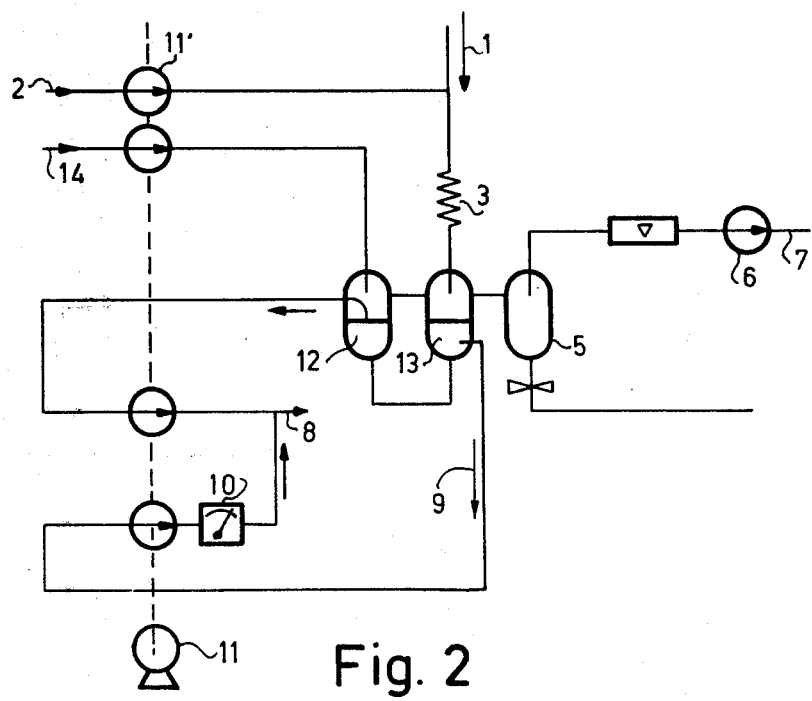

An embodiment of the invention will now be described, by way of example, with reference to the accompanying diagrammatic drawings, in which FIG. 1 shows schematically a prior-art apparatus and FIG. 2 shows schematically an apparatus according to the invention.

Referring now to FIG. 1, reference numeral 1 denotes the incoming stream of gas to be analysed whilst 2 denotes the constant supply of absorption liquid. In an absorbing member 3 the absorption liquid and the gas to be analysed are in contact with one another for a comparatively long period of time so that at least a constant fraction of the component to be determined dissolves in the absorption liquid. In an embodiment of an application of the apparatus the content of hydrogen fluoride gas in polluted air is measured.

The absorption liquid charged with the component to be measured and the measuring gas enter a liquid separator 4 from which the gas is aspirated by means of a pump 6 via a droplet trap 5 and a flowmeter. The gas is discharged from the apparatus at 7, the liquid at 8. The liquid in the liquid separator is drawn off from a suction opening so that the liquid is maintained at a constant level. The liquid charged with the component to be analysed is conducted to a detector 10 through a conduit 9. Care is taken to ensure that the amount drained from the separator at 9 is less than the supply from the absorption member 3. A chain of coupled pumps 11 to 11' ensures the required movement at constant speed of the various liquid streams.

The apparatus according to the invention is shown schematically in FIG. 2. Elements of this apparatus which are identical with those of FIG. 1 are designated by the same reference numerals.

The liquid separator comprises two communicating reservoirs 12 and 13 which communicate with one another both for the liquid phase and for the gas phase. From 14 pure solvent of the absorption liquid is supplied to the reservoir 12 whilst the absorption liquid charged with the component to be determined and the measuring gas are supplied to the reservoir 13. The reservoir 12 is provided with the draining outlet through which the liquid is drawn off to 8. Care is taken to ensure that the amount discharged from the separator at 9 is smaller than the overall supply of liquid from 3 and 14 but greater than the supply from 3 alone.

What is claimed is:

1. Apparatus for continuous sampling for use in a continuous determination of a gaseous component in a gas mixture, in which apparatus at least the component to be determined is absorbed in a liquid and determination is performed on the resulting doped liquid, which apparatus comprises an absorption member to which a constant stream of sample gas and a constant stream of absorption liquid are supplied and in which the two streams are brought into contact with one another, and a passage to a liquid separator having a constant liquid level by means of a suction opening, a gas outlet being provided above the liquid level and a liquid outlet being provided below this level, whilst care is taken to ensure that at any instant the amount discharged to the liquid separator is less than the amount supplied, whilst liquid is discharged from the separator and supplied to a detector with a constant flow quantity, characterized in that the liquid separator comprises two reservoirs which communicate with another both for the gas phase and for the liquid phase, the supply conduit from the absorption member opening into one reservoir whilst the suction opening of the level-regulator is disposed in the other reservoir, to which latter reservoir a constant stream of pure solvent of the absorption liquid is supplied, the total quantity of discharged liquid to be analized being smaller than the overall supply but greater than the supply from the absorption member alone.

* * * * *